US009255112B1

(12) United States Patent
Frąckowiak et al.

(10) Patent No.: US 9,255,112 B1
(45) Date of Patent: Feb. 9, 2016

(54) (DIMETHYLVINYLGERMOXY) HEPTASUBSTITUTED SILSESQUIOXANES AND THE METHOD OF THEIR SYNTHESIS

(71) Applicant: ADAM MICKIEWICZ UNIVERSITY, Poznań (PL)

(72) Inventors: Dawid Frąckowiak, Poznań (PL); Patrycja Żak, Poznań (PL); Bogdan Marciniec, Swarzędz (PL)

(73) Assignee: ADAM MICKIEWICZ UNIVERSITY, Poznan (PL)

( * ) Notice: Subject to any disclaimer, the term of this patent is extended or adjusted under 35 U.S.C. 154(b) by 0 days.

(21) Appl. No.: 14/677,118

(22) Filed: Apr. 2, 2015

(30) Foreign Application Priority Data

Feb. 11, 2015 (PL) .......................... 411195

(51) Int. Cl.
*C07F 7/30* (2006.01)

(52) U.S. Cl.
CPC ........................ *C07F 7/30* (2013.01)

(58) Field of Classification Search
USPC ............................ 556/434, 443, 460, 467, 10
See application file for complete search history.

(56) References Cited

U.S. PATENT DOCUMENTS 6,248,852 B1   6/2001  Risen, Jr. et al.
2010/0081837 A1*  4/2010  Saito ........................... 556/413

OTHER PUBLICATIONS

Marciniec; Organometallics; 2015, 34, 3950-3958; published on Aug. 3, 2015.*

* cited by examiner

*Primary Examiner* — Sudhakar Katakam
*Assistant Examiner* — Pancham Bakshi
(74) *Attorney, Agent, or Firm* — Oliff PLC

(57) ABSTRACT

(Dimethylvinylgermoxy)heptasubstituted silsesquioxanes of the formula 1,

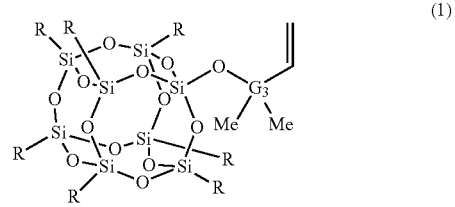

(1)

in which the substituents R are equal to one another and represent: a linear or branched $C_2$ to $C_8$ alkyl group; a cyclopentyl or cyclohexyl group; a phenyl group; and the method of their synthesis.

5 Claims, No Drawings

(DIMETHYLVINYLGERMOXY) HEPTASUBSTITUTED SILSESQUIOXANES AND THE METHOD OF THEIR SYNTHESIS

The invention relates to (dimethylvinylgermoxy)heptasubstituted silsesquioxanes and the method of their synthesis.

The purpose of the invention was to synthesize molecules of (dimethylvinylgermoxy)heptasubstituted silsesquioxanes, i.e. silsesquioxanes having seven alkyl or aryl substituents and one dimethylvinylgermoxyl group which are bound directly to silicon atoms belonging to the silsesquioxane skeleton.

The invention relates to cage (dimethylvinylgermoxy)heptasubstituted silsesquioxanes of the formula 1,

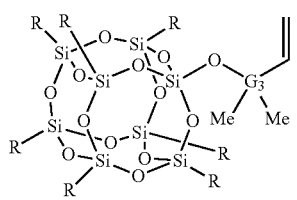

(1)

in which the substituents R are equal to one another and represent:
   a linear or branched $C_2$ to $C_8$ alkyl group
   a cyclopentyl or cyclohexyl group
   a phenyl group In the second aspect, the invention relates to a method of synthesis of cage (dimethylvinylgermoxy)heptasubstituted silsesquioxanes of the general formula 1,

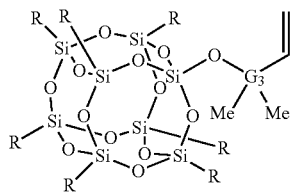

(1)

in which the substituents R are equal to one another and represent:
   a linear or branched $C_2$ to $C_8$ alkyl group
   a cyclopentyl or cyclohexyl group
   a phenyl group,
the method comprising the reaction between a cage monosilanol POSS of the formula 2,

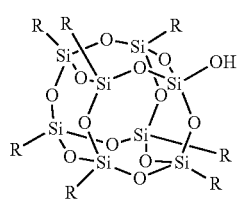

(2)

in which R have the meaning defined above, and chlorodimethylvinylgermane of the formula 3,

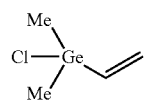

(3)

in the presence of an amine and a compound binding hydrogen chloride released during the reaction.

The reaction is carried out in an organic solvent selected from the group consisting of ethers, saturated hydrocarbons and aromatic hydrocarbons. It is advantageous to use solvents selected from the group consisting of THF, hexane, pentane, diethyl ether and benzene.

Due to the properties of chlorodimethylvinylgermane, the reaction of synthesis of (dimethylvinylgermoxy)heptasubstituted silsesquioxanes should preferably be carried out in anhydrous conditions. Conducting the reaction in a moisture-containing medium leads to a major decrease in the yield of the process in connection with the reaction of chlorodimethylvinylgermane with water, leading to 1,1,3,3-tetramethyl-1,3-divinyldigermoxane. Due to the high reactivity of chlorodimethylvinylgermane towards water, the reagents and solvents should be dried so as to avoid the formation of by-products which can be very difficult or even impossible to separate from the product proper.

The reaction can be carried out in an air atmosphere, however in order to obtain more advantageous yields, the reaction should preferably be carried out in an atmosphere of an inert gas, e.g. argon or nitrogen.

The reaction can be carried out over a broad temperature range, however it is advantageously carried out at room temperature, since higher temperatures do not have a significant effect on increasing the yield, whereas reducing the temperature has a substantial effect on decreasing the yield of the reaction.

The amine can be selected from trialkyl- or dialkylamines, and it is particularly advantageous to use triethylamine. The amine plays the role of a reagent initiating the reaction between heptasubstituted monosilanol POSS and chlorodimethylvinylgermane. At the same time, the amine can perform the function of a compound binding hydrogen chloride which is a product of the condensation reaction.

The agent binding hydrogen chloride can be any compound dissolving in the reaction environment and forming a stable salt with chloride anions.

The synthesis reaction takes place at the molar ratio of the reagents [chlorodimethylvinylgermane]:[heptasubstituted monosilanol POSS] of 1:1. It is advantageous to use a slight excess of chlorodimethylvinylgermane. The reaction involves the use of an amine in an amount not less than one equivalent relative to heptasubstituted monosilanol POSS, however when the amine is also used as an agent binding hydrogen chloride, it is used in an amount not less than 1.2 equivalents relative to chlorodimethylvinylgermane.

It is advantageous to carry out the reaction by applying the following sequence of adding reagents: first, dissolve heptasubstituted monosilanol POSS in a selected solvent, then add an amine and mix the entire contents intensively for several minutes, and afterwards add chlorodimethylvinylgermane, advantageously in small portions. A change in the sequence of adding reagents may result in reduced reaction yield.

The products are purified in the following manner:
  a) if the reaction is carried out in saturated hydrocarbons (e.g. pentane, hexane) or aromatic hydrocarbons (e.g. benzene, toluene), the formed ammonium salt is filtered off, and the solvent is evaporated under reduced pressure. The products, which have the form of powders, are precipitated in a cooled methanol/water mixture (to wash out traces of ammonium salts which can potentially interfere with further functionalization of (dimethylvinylgermoxy)heptasubstituted silsesquioxane; the water/methanol volume ratio should be within the range from 75:25 to 80:20; following which it is filtered off and finally dried under reduced pressure.

b) if the reaction is carried out in ethers, the solvent should be evaporated under reduced pressure and then the residue should be combined with a small amount of a light saturated hydrocarbon (e.g. pentane, hexane or petroleum ether), in which the reaction product is dissolved for the purpose of separation from residues of the ammonium salt whose solubility in ether solvents is slightly higher than in hydrocarbons. The ammonium salt precipitate is then filtered off, and the solvent is removed from the filtrate under reduced pressure. The further procedure is the same as described in subsection a).

Cage (dimethylvinylgermoxy)heptasubstituted silsesquioxanes according to the invention have applications, among others, as fillers for polymers having specific optical properties. On the one hand, the inorganic silicon-oxygen siloxane core present in these compounds is responsible for their good thermal and mechanical properties that determine their application as fillers and is also responsible for their high optical transparency, which is significant in the aspect of their application in optoelectronics (e.g. as OLEDs) and catalysis, and primarily electronics.

On the other hand, the presence of the Ge—O—Si group significantly affects the optical properties of the compounds since, as Honore et al. (W. M. Risen, Jr., Y. Z. Wang, A. Honore, U.S. Pat. No. 6,248,852, 2001) have shown, the introduction of a Ge—O—Si group into siloxane backbone has a substantial effect on increasing the value of the refractive index in relation to analogous siloxanes that do not contain a germanium atom, which is why such materials are applied in the manufacture of specialized spin glasses, glass films, microlenses, lasers and adhesive layers.

The compounds according to the invention combine the characteristics of silsesquioxane derivatives (as they preserve the identical skeleton structure of the siloxane fragment) and, at the same time, due to the introduction of a vinylgermoxyl group as a substituent of the silsesquioxane cage, they exhibit specific optical properties and can be used for the manufacture of precursors for elements of composite optical materials or substrates in the synthesis of functionalized oligomers with specific electronic properties which are used e.g. in optoelectronics.

The method according to the invention is presented in examples given below which do not limit the applications of the invention.

The analysis of products was performed with:
the $^1$H and $^{13}$C-NMR spectra were recorded on a Varian Gemini 300 spectrometer at 300 and 75 MHz,
the $^{29}$Si NMR spectra were recorded on a Varian Avance 600 spectrometer at 119.203 MHz,
the mass spectra were recorded on a 4000 Q TRAP system from Applied Biosystems.

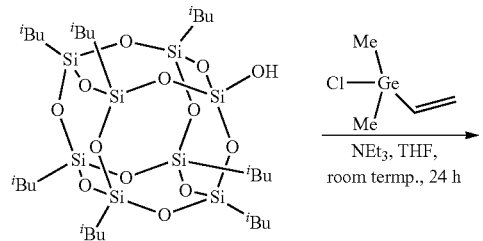

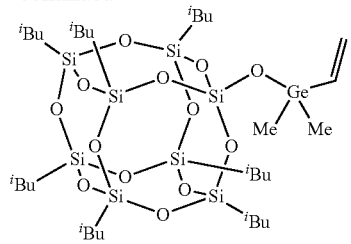

A two-necked flask with a volume of 100 mL, equipped with a reflux condenser and an adapter for introducing inert gas, was loaded in an argon atmosphere with heptaisobutylmonosilanol POSS (1.5 g, 1.8 mmol), deoxygenated and dried tetrahydrofuran (50 mL), and triethylamine (0.33 mL, 2.73 mmol). Then, chlorodimethylvinylgermane (0.4 g, 2.42 mmol) was added very slowly drop by drop at room temperature into the reaction mixture, whereupon the ammonium salt was precipitated. The suspension was mixed for 24 h at room temperature, after which THF was evaporated under reduced pressure. The residues were combined with 20 mL of hexane, and then filtered in air on a glass sinter connected to a membrane pump. The precipitate was washed with small portions of hexane (3×10 mL), and the filtrate was evaporated until dryness. The residues were then combined with a cold aqueous solution of methanol; white precipitate was formed and was filtered on a glass sinter funnel. (Dimethylvinylgermoxy) heptaisobutylsilsesquioxane in the form of white powder was obtained with a yield of 85%.

$^1$H NMR (CDCl$_3$, δ, ppm): 0.50 (s, 6H, —Ge(CH$_3$)$_2$—); 0.56-0.65 (m, 14H, CH$_2$); 0.86-1.03 (m, 42H, CH$_3$); 1.77-1.95 (m, 7H, CH); 5.75 (dd, 1H, J$_{HH}$=20.1, 2.9 Hz, CH═CH$_2$); 6.01 (dd, 1H, J$_{HH}$=13.7, 2.9 Hz, CH═CH$_2$); 6.32 (dd, 1H, J$_{HH}$=20.1, 13.7 Hz, CH═CH$_2$)

$^{13}$C NMR (CDCl$_3$, δ, ppm): 0.62 (—Ge(CH$_3$)$_2$—); 22.46, 22.53 (CH$_2$); 23.80, 23.86 (CH); 25.68, 25.73 (CH$_3$); 131.33 (═CH$_2$); 138.31 (═CH—Ge)

$^{29}$Si NMR: (CDCl$_3$, δ, ppm): −67.30; −67.90; −105.73

MS (ASAP): m/z (%):833.26 (57); 834.26 (40); 835.26 (29); 959.24 (34); 961.24 (68); 963.24 (100); 964.24 (69); 965.24 (57); 966.24 (30)

HRMS (ASAP) for C$_{32}$H$_{73}$GeO$_{13}$Si$_8$: calcd 963.2417. found 963.2432;

Elemental analysis: calcd (%) for C$_{32}$H$_{72}$GeO$_{13}$Si$_8$: C: 39.94; H: 7.54; found 39.83; H: 7.57.

The invention claimed is:
1. Cage (dimethylvinylgermoxy)heptasubstituted silsesquioxanes of the formula 1,

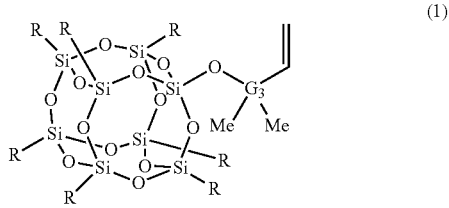

(1)

in which the substituents R are equal to one another and are selected from the group consisting of a linear or branched C$_2$ to C$_8$ alkyl group, a cyclopentyl group, a cyclohexyl group and a phenyl group.

2. A method of synthesis of the cage (dimethylvinylgermoxy)heptasubstituted silsesquioxanes of claim 1, the method comprising a reaction between a cage monosilanol POSS of the formula 2,

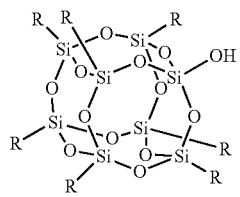
(2)

in which R have the meaning defined above, and chlorodimethylvinylgermane of the formula 3,

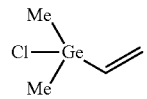
(3)

in the presence of an amine and a compound binding hydrogen chloride released during the reaction.

3. The method, as claimed in claim 2, wherein the reaction is carried out in the presence of a trialkyl- or dialkylamine.

4. The method, as claimed in claim 3, wherein the amine is used in an amount not less than one equivalent relative to heptasubstituted monosilanol POSS.

5. The method, as claimed in claim 3, wherein the reaction is carried out in the presence of triethylamine.

* * * * *